(12) United States Patent
Lang et al.

(10) Patent No.: US 7,132,538 B2
(45) Date of Patent: Nov. 7, 2006

(54) ISOLATION OF HIGH-PURITY TRIETHYLENEDIAMINE (TEDA) BY DISTILLATION

(75) Inventors: Ortmund Lang, Quirnbach (DE); Bernd Rumpf, Hockenheim (DE); Matthias Frauenkron, Freinsheim (DE); Marco Bosch, Mannheim (NL); Helmut Berrsche, Hassloch (DE); Anton Meier, Birkenheide (DE)

(73) Assignee: BASF Aktiengesellschaft, Ludwigshafen (DE)

(*) Notice: Subject to any disclaimer, the term of this patent is extended or adjusted under 35 U.S.C. 154(b) by 295 days.

(21) Appl. No.: 10/829,176

(22) Filed: Apr. 22, 2004

(65) Prior Publication Data

US 2004/0220406 A1 Nov. 4, 2004

(30) Foreign Application Priority Data

Apr. 29, 2003 (DE) .............................. 103 19 159

(51) Int. Cl.
*C07D 487/00* (2006.01)

(52) U.S. Cl. .................................................. 544/352
(58) Field of Classification Search ............... None
See application file for complete search history.

(56) References Cited

U.S. PATENT DOCUMENTS

| | | | |
|---|---|---|---|
| 3,297,701 A | 1/1967 | Brader et al. | 260/268 |
| 6,147,208 A * | 11/2000 | Achhammer et al. | 540/538 |
| 6,552,194 B1 | 4/2003 | Lang et al. | 544/352 |
| 6,627,756 B1 | 9/2003 | Riechers et al. | 544/352 |

OTHER PUBLICATIONS

Lestak and Smith, "The Control of Dividing Wall Column" Chemical Engineering Research and Design, vol. 71(A3), p. 307 (1993).*
Schultz M A et al.: "Reducing Costs with Dividing-Wall Columns", CEP Magazine, 'Online! Bd. 98, NR. 5, 2002, pp. 64-71; XP00291891.
Lestak et al.: "Advanced Distillation Saves"; Chemical Engineering, McGraw-Hill, Albany, NY, US, Bd. 7, Jul. 1997, pp. 72-76; XP001156299.
Kaibel G.: "Distillation Columns with Vertical Partitions", Chemical Engineering and Technology, Weinheim, DE, Bd. 10, 1987, pp. 92-98; XP002939161.

* cited by examiner

*Primary Examiner*—Zachary C. Tucker
(74) *Attorney, Agent, or Firm*—Novak Druce & Quigg, LLP

(57) ABSTRACT

Process for purifying triethylenediamine (TEDA) by disillation, in which the fractionation is carried out in a dividing wall column.

4 Claims, 1 Drawing Sheet

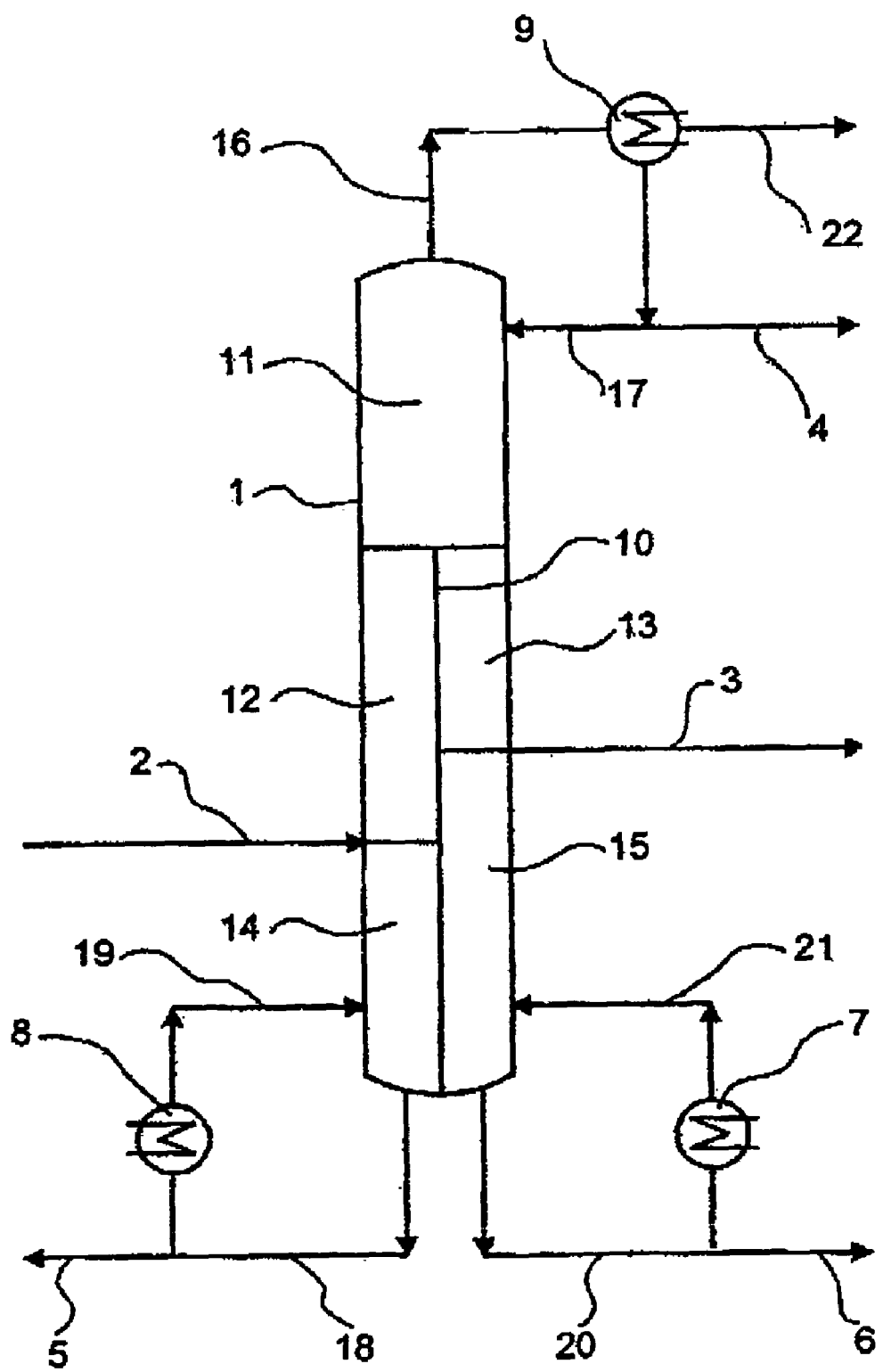

ISOLATION OF HIGH-PURITY TRIETHYLENEDIAMINE (TEDA) BY DISTILLATION

The present invention relates to an improved process for isolating triethylenediamine (=TEDA=DABCO®=1,4-diazabicyclo[2.2.2]octane) and solutions thereof by distillation.

TEDA, which is a solid under normal conditions, is an important catalyst for the production of polyurethane foams.

For this and other uses, a pure, essentially odor-free and pure white TEDA which has little discoloration, e.g. has a very low APHA color number (DIN-ISO 6271), and retains these properties even over relatively long storage times (e.g. 6, 12 or more months) is desirable.

Various processes for preparing and purifying TEDA are known. DE-A 19962455 describes a process for preparing TEDA in which TEDA is vaporized and the gaseous TEDA is passed into a liquid solvent.

DE-A 10100943 discloses a process for preparing TEDA in which, inter alia, the solvent or diluent has specific properties.

DE-A 19933850 describes a process for purifying TEDA in which the TEDA is fractionally distilled and then passed into a liquid solvent.

In the industrial preparation of TEDA, TEDA is usually isolated from crude TEDA in batch distillation apparatuses or in two or more continuously operated distillation apparatuses. This is described, for example, in DE-A 19933850 (page 3, lines 30 to 43).

The secondary components still present after the preliminary removal of low boilers and high boilers are, however, partly decomposed in the pure distillation in a conventional distillation procedure and can lead to the formation of undesirable by-products which can adversely affect the product quality of the TEDA. A large process engineering outlay is therefore necessary to counter the disadvantages indicated and meet the usually high product quality requirements in respect of parameters such as color, color stability, odor and product purity.

It is an object of the present invention to find an improved process for purifying crude TEDA which makes it possible for high-purity TEDA of high quality to be isolated in a simple and inexpensive way.

We have found that this object is achieved by a process for purifying triethylenediamine (TEDA) by distillation, in which the fractionation is carried out in a dividing wall column.

Dividing wall columns are generally known distillation columns and are comprehensively described in the literature. They have vertical dividing walls which prevent transverse mixing of liquid and vapor streams in parts of the column. The dividing wall usually comprises a flat metal sheet and divides the column longitudinally in its middle region into an inflow section and an offtake section. In the process of the present invention, the mixture to be fractionated, viz. the crude TEDA, is fed into the inflow section of the dividing wall column and the product, vz. the pure TEDA, is taken off in liquid or gaseous form from the offtake section.

The use a dividing wall column would in the case of the present materials system not have been taken into consideration by a person skilled in the art, since, as indicated above, undesirable by-products which can adversely affect the product quality are formed as a result of decomposition processes. For this reason, only a two-stage distillation would have been seen as likely to be successful in the case of this materials system because of the high TEDA quality generally required. In the case of a dividing wall column, increased disadvantages would have been expected in this respect. However, it has been found that high-purity TEDA can be obtained in a simple and economical way by means of the process of the present invention.

In the process of the present invention, the dividing wall is generally arranged in the longitudinal direction of the column to form an upper combined column region and/or a lower combined column region, an inflow section and an offtake section. In a preferred embodiment, the dividing wall continues down to the bottom of the column so as to form a combined region only in the upper region of the column. This has the advantage that low boilers formed by decomposition of high boilers or secondary components are conveyed upward only in the lower part of the column in which the feed point is located. This avoids undesirable discharge of these low boilers via the side offtake.

The process is generally carried out continuously.

The dividing wall column is preferably equipped with two bottom vaporizers and a condenser at the top of the column.

In the process of the present invention, the residence time in the bottom vaporizer and the associated piping system is advantageously limited to from 1 to 15 minutes, preferably from 1 to 5 minutes. In this way, the required TEDA quality is achieved in the offtake section despite decomposition of high boilers and of secondary components.

In a preferred process variant, the ratio of liquid runback at the upper end of the dividing wall into the inflow section and offtake section of the column is regulated in the range 1:1–5, preferably a ratio of 1:1.4–2. This is preferably carried out by collecting the liquid at the upper end of the dividing wall and introducing it into the inflow and offtake sections of the column in the abovementioned ratio by means of a regulating or setting device. This ensures a lower energy consumption.

The process of the present invention is preferably carried out at a pressure at the top of the column of from 0.5 to 5 bar, preferably from 0.5 to 1.5 bar.

A temperature regulation is preferably provided in the upper combined column region with a measurement point below the uppermost theoretical plate, preferably in the third theoretical plate counted from the top, which utilizes the distillate flow, the reflux ratio or preferably the amount of runback as setting parameters. This ensures stable operation of the column, resulting in a further improvement in the achievable product purity.

In a further process variant, a temperature regulation is provided in the lower column region of the inflow section with a measurement point above the bottom most theoretical plate, preferably on the second theoretical plate counted from the bottom, which utilizes the amount of bottoms taken off as setting parameter, either in addition to or as an alternative to the temperature regulation in the upper part of the column. This additional measure achieves a further improvement in stable operation of the column.

Furthermore, as an additional or alternative measure, a level regulation which utilizes the amount taken off at the side offtake as setting parameter can be provided at the bottom of the column in the inflow section and/or the offtake section.

The dividing wall column used in the process of the present invention has from about 20 to 70 theoretical plates, preferably from 30 to 50 theoretical plates.

The feed point for the crude TEDA is preferably located on a theoretical plate between the 5th and 30th theoretical plates, preferably between the 10th and 20th theoretical plates.

The side offtake for the pure TEDA is preferably located between the 2nd to 20th theoretical plates, preferably between the 3rd to 20th theoretical plates.

The dividing wall is preferably installed in the column between the bottom of the column and the 30th theoretical plate counted from the bottom, particularly preferably between the bottom of the column and the 20th theoretical plate. In a preferred embodiment, the dividing wall is installed centrally.

The separation-active internals are in principle subject to no restrictions; preference is given to ordered packing or trays.

BRIEF DESCRIPTION OF THE DRAWING

The invention is illustrated below with the aid of the FIGURE and an example.

The FIGURE shows a dividing wall column (1) having a dividing wall (10) which divides the dividing wall column into a combined upper column region (11), an inflow section (12), (14) with enrichment section (12) and stripping section (14), an offtake section (13), (15) with a stripping section (15) and an enrichment section (13). The crude TEDA enters the dividing wall column via the feed line (2) between the column sections 12 and 14. The pure TEDA is taken off, preferably in gaseous form, via the side offtake (3) between the column sections 13 and 15. The vapor stream obtained at the top of the column is conveyed via line (16) to the condenser (9), which may be supplemented by an aftercooler, where it is partly condensed and is divided into the runback stream (17) and the distillate stream (4). The uncondensed fraction from the condenser (9) comprises the low-boiling impurities and is taken off in gaseous form via line (22). At the lower end of the inflow and offtake sections of the column, the liquid is conveyed via the lines (18), (20) to the vaporizers (7), (8), partly vaporized and recirculated via the lines (19), (21) to the column. High-boiling impurities are taken off via lines (5), (6). The vaporizers (7), (8) can be configured as natural convection vaporizers or as forced circulation vaporizers; in the latter case, additional circulation pumps for the liquid streams are necessary. To avoid undesirable decomposition products, it is particularly advantageous to use falling film evaporators or thin film evaporators in the place of forced circulation vaporizers, since shorter residence times are possible using this type of construction. To reduce the residence times of the liquid in the vaporizer system, it is advantageous to install the level control not in the lower end of the column but in the lines for the liquid (18), (20).

The process of the present invention makes it possible for pure triethylenediamine (TEDA) and solutions thereof to be isolated in a simple, economical and efficient way. Products (TEDA) of high quality in respect of color, color stability, odor and purity are prepared in the process.

EXAMPLE 1

A crude TEDA stream of 280 kg/h having a temperature of 167° C. was fed in liquid form onto the 8th theoretical plate of a dividing wall column 1 having a total of 30 theoretical plates. The crude TEDA had the following composition:

| | |
|---|---|
| Water: | 0.1% by weight |
| Low boilers: | 1.4% by weight |
| Piperazine: | 34.0% by weight |
| Ethylpiperazine: | 0.9% by weight |

-continued

| | |
|---|---|
| TEDA: | 58.2% by weight |
| Aminoethylpiperazine: | 2.0% by weight |
| Residue: | 3.4% by weight |

The dividing wall 10 extended from the bottom of the column to the 20th theoretical plate. The side offtake 3 was located on the 3rd theoretical plate. The column was operated at a pressure at the top of 1.2 bar and a pressure at the bottom of 1.3 bar. Condensation at the top of the column was carried out at a temperature of 154° C. A gaseous stream 22 comprising low boilers and having a flow of 4 kg/h was taken off from the condenser 9. A substream 4 of 100 kg/h was taken off from the condensed stream. The high-boiling impurities 5, 6 were taken off in an amount of 19 kg/h at 230 and 180° C. respectively at the bottom of the column. At the side offtake 3, the desired product TEDA having an assay of 99.9% by weight was obtained in gaseous form at a temperature of 181° C. in an amount of 157 kg/h. The division ratio for the liquid at the upper end of the dividing wall 10 between inflow section and offtake section was 1:1.5

EXAMPLE 2

Example 1 is repeated with a crude TEDA stream of 500 kg/h. A gaseous stream 22 comprising low boilers and having a flow of 5 kg/h was taken off from the condenser 9. A substream 4 of 180 kg/h was taken off from the condensed stream. The high-boiling impurities 5, 6 were taken off in an amount of 32 kg/h at 230 and 180° C. respectively at the bottom of the column. At the side offtake 3, the desired product TEDA having an assay of 99.9% by weight was obtained in gaseous form at a temperature of 181° C. in an amount of 283 kg/h. The division ratio for the liquid at the upper end of the dividing wall 10 between inflow section and offtake section was 1:1.5.

EXAMPLE 3

A crude TEDA stream of 100 kg/h having a temperature of 167° C. was fed in liquid form onto the 4th theoretical plate of a dividing wall column 1 having a total of 24 theoretical plates. The crude TEDA had the following composition:

| | |
|---|---|
| Water: | 0.1% by weight |
| Low boilers: | 1.4% by weight |
| Piperazine: | 50.0% by weight |
| Ethylpiperazine: | 0.9% by weight |
| TEDA: | 42.2% by weight |
| Aminoethylpiperazine: | 2.0% by weight |
| Residue: | 3.4% by weight |

The dividing wall 10 extended from the bottom of the column to the 18th theoretical plate. The side offtake 3 was located on the 2nd theoretical plate. The column was operated at a pressure at the top of 1.2 bar and a pressure at the bottom of 1.3 bar. Condensation at the top of the column was carried out at a temperature of 154° C. A gaseous stream 22 comprising low boilers and having a flow of 4 kg/h was taken off from the condenser 9. A substream 4 of 50 kg/h was taken off from the condensed stream. The high-boiling impurities 5, 6 were taken off in an amount of 9 kg/h at 230 and 180° C. respectively at the bottom of the column. At the side offtake 3, the desired product TEDA having an assay of 99.9% by weight was obtained in gaseous form at a temperature of 181° C. in an amount of 37 kg/h. The division ratio for the liquid at the upper end of the dividing wall 10 between inflow section and offtake section was 3:1.

The process of the present invention enables the distillation of crude TEDA to produce pure TEDA conforming to the required specification to be carried out at a cost saving of 20% compared to the conventional 2-stage distillation process.

We claim:

1. A process for purifying triethylenediamine (TEDA) by distillation, wherein the fractionation is carried out in a dividing wall column wherein a dividing wall column whose internal dividing wall continues down to the bottom so as to form separate chambers in the lower region of the column is used.

2. A process as claimed in claim 1, wherein the ratio of runback at the upper end of dividing wall into the inflow and offtake sections of the column is regulated in the range from 1;1 to 1:5.

3. A process as claimed in claim 1, wherein the residence time in the bottom vaporizer is limited to from 1 to 15 minutes.

4. A process as claimed in claim 1, wherein the dividing wall column is operated at a pressure at the top of from about 0.5 to 5 bar.

* * * * *